United States Patent [19]

Edison et al.

[11] Patent Number: 4,737,400

[45] Date of Patent: Apr. 12, 1988

[54] METHOD FOR MAKING ELASTIC BANDAGING MATERIAL

[75] Inventors: Charles J. Edison, Swampscott; Thomas S. Murphy, Jr., Marblehead; Raymond H. Willingham, Gloucester, all of Mass.

[73] Assignee: Expandover, Inc., Marblehead, Mass.

[21] Appl. No.: 748,693

[22] Filed: Jun. 25, 1985

Related U.S. Application Data

[63] Continuation of Ser. No. 543,480, Oct. 20, 1983, abandoned.

[51] Int. Cl.⁴ .............................................. D03D 3/00
[52] U.S. Cl. ................................. 428/230; 428/231; 428/247; 428/248; 428/249; 428/252; 428/258; 428/259; 428/261; 428/264; 428/265; 428/266; 428/343; 428/352; 428/354; 428/906; 427/381; 427/389.9; 427/394
[58] Field of Search ...................... 427/381, 389.9, 394

[56] References Cited

U.S. PATENT DOCUMENTS 3,618,754 11/1971 Hoey ................................... 428/231
4,366,814 1/1983 Riedel ................................ 428/230
4,424,808 1/1984 Schäfer ............................... 428/231

*Primary Examiner*—Marion C. McCamish
*Attorney, Agent, or Firm*—I. Stephen Samuels

[57] ABSTRACT

A method of producing breathable, conformable, elastic, pressure-sensitive, permanently tacky, adhesive bandaging material from a fabric which has been formed by interweaving essentially non-stretch filling yarns with stretch and non-stretch warp yarns, said method comprising conveying a continuous web of said fabric in a substantially relaxed condition, applying steam to the relaxed fabric, and applying an adhesive layer to the back side of the relaxed fabric.

A breatable, conformable, elastic, pressure-sensitive, permanently tacky, adhesive bandaging material comprising a fabric formed by essentially non-stretch filling yarns interwoven with stretch and non-stretch warp yarns, the fabric normally being in a relaxed condition, an adhesive applied in a level layer to the entire back side of the relaxed fabric such that, in its relaxed state, the bandaging material has an adhesive layer which has a smooth exposed surface and a substantially uniform depth throughout, and such that, in its stretched state, the adhesive bandaging material has an adhesive layer which has a non-uniform, discontinuous surface and a depth which varies from being relatively great where the non-stretch warp yarns extend to the back side of the fabric to being relatively slight or even zero where the non-stretch warp yarns extend away from the back side of the fabric.

40 Claims, 2 Drawing Sheets

METHOD FOR MAKING ELASTIC BANDAGING MATERIAL

This is a continuation of co-pending application Ser. No. 543,480 filed on Oct. 20, 1983, now abandoned.

BACKGROUND OF THIS INVENTION

This invention is an improvement over Hoey, U.S. Pat. No. 3,618,754, issued Nov. 9, 1971, which is also the closest prior art of which the applicants of the present invention are aware. Hoey discloses a continuous fabric web which is conveyed in a fully stretched condition and which is adhesivecoated in such stretched condition using high heat calender rolls. Hoey's method causes two problems. First, by applying the adhesive to a fully stretched fabric, the bandaging material has poor breathability when used. That is, in use, the bandaging material is stretched and the adhesive layer is thick and uniform in depth, preventing air passage through the adhesive layer. Second, by heating the fully stretched elastomeric warp yarns to between 240° and 240° F., the stretch warp yarns lose a great deal of their power of recovery and a great deal of their elasticity.

This is precisely the opposite way in which applicants' bandaging material is produced, i.e. applicants' fabric is first steamed and is then coated with an adhesive layer, both steps occurring while the fabric is being conveyed in a fully relaxed condition. Applicants avoid using high heat throughout their process.

Because of this difference in the methods by which Hoey's bandaging material and applicants' bandaging material are produced, the resulting materials have different physical characteristics. Hoey does not initially steam his fabric whereas applicants do steam their fabric. This steaming step exfoliates and spreads the interwoven filling and warp yarns of applicants' fabric and also expands and loosens non-stretch yarns thereby facilitating a fuller retraction of applicants' stretch warp yarns. As a result, applicants' bandaging material strongly and repeatedly recovers to its original relaxed length after being stretched, whereas the Hoey bandaging material has a weaker snap-back and has reduced elasticity especially after an extended period of full stretch.

Furthermore, applicants' fabric preferably receives an acrylic polymer coating which improves the tearability of applicants' bandaging material and which inhibits fraying at the edges of the material. Hoey's material does not receive such a coating.

For all of the foregoing reasons, applicants' bandaging material is an improvement over the Hoey material and is a decided advance in the art.

SUMMARY OF THE INVENTION

This invention is a method of producing rolls of bandaging material, and is also the bandaging material itself. The method comprises the use of a fabric which is conveyed in a continuous web in a relaxed condition. Steam is applied to the relaxed fabric, the fabric is dried with low heat, a release coating and/or a non-fray coating is applied to the fabric, a layer of adhesive is applied to the back side of the conveyed relaxed fabric, and the adhesive is dried with low heat. The material is then wound into a roll and is then slit into a plurality of rolls having the desired roll width.

The bandaging material itself is made from a fabric formed by non-stretch filling yarns interwoven with interspersed stretch and non-stretch warp yarns, a release coating and/or a non-fray coating covers the entire face side of the fabric, a level layer of adhesive covers the entire back side of the relaxed fabric to form a bandaging material which, in its relaxed state, has an adhesive layer which has a smooth exposed surface and a substantially uniform depth throughout and which, in its stretched state, has an adhesive layer which has a non-uniform, discontinuous surface and a depth which is relatively great where the non-stretch warp yarns extend to the back side of the fabric and which is relatively slight or zero where the non-stretch warp yarns extend away from the back side of the fabric. The material is wound on a core in roll form.

DESCRIPTION OF THE DRAWINGS

FIG. 4 is a sectional view taken along line 4—4 in FIG. 2.

DESCRIPTION OF THE PREFERRED METHOD AND MATERIAL

Figure 1:
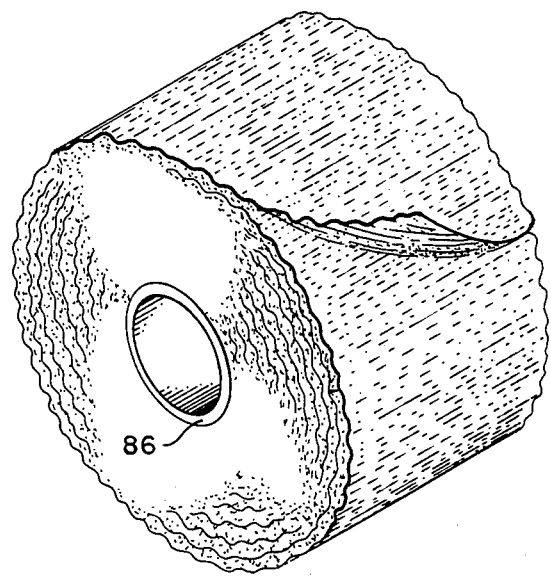
FIG. 1 is a perspective view of the roll of bandaging material of this invention.

In order to produce the roll of bandaging material shown in FIG. 1, applicants start with a continuous web of rolled fabric 10. An example of a suitable fabric is one which has been formed by the interweaving of essentially non-stretch filling yarns 12, such as cotton, with warp yarns consisting of non-stretch warp yarns 14, such as cotton, interspersed with stretch warp yarns 16, such as corespun Dupont Lycra spandex filaments around which are wrapped fibers of cotton and polyester. An example of a suitable warp yarn arrangement is one in which two ends of cotton warp yarn lie next to one end of spandex core stretch warp yarn in a repeating pattern. The spandex core stretch warp yarns, when stretched, have an average float length on the back side of the fabric which exceeds the average float length of the cotton warp yarns on the back side. For example, each end of stretch warp yarn 16 floats over five picks of cotton filling yarn 12 on the back side, then weaves under, over, and under three picks of cotton filling yarn 12, then floats over five picks of cotton filling yarn 12 in a repeating pattern. Of course, this is but one example of a suitable fabric, and the materials and the weaving pattern could be modified in a wide variety of ways.

Figure 2:
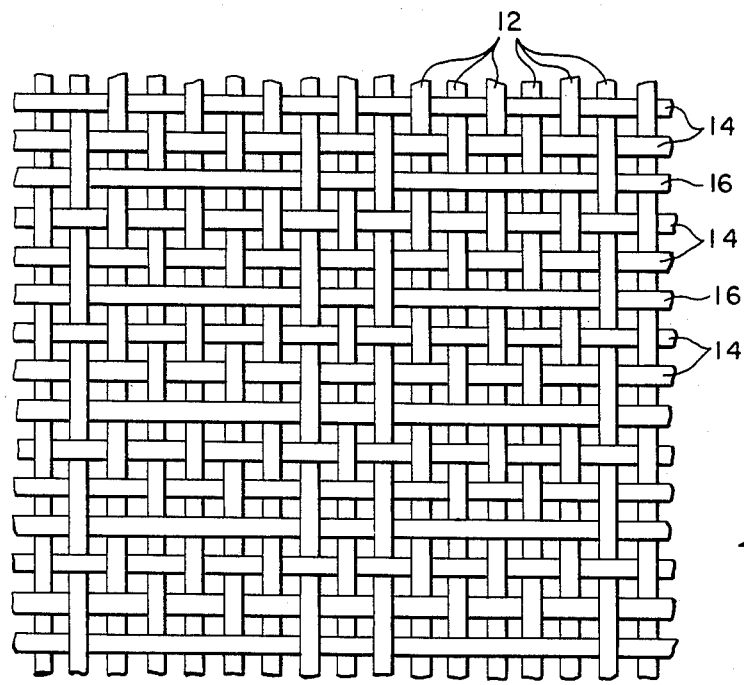
FIG. 2 is a schematic bottom plan view on an enlarged scale of the stretched fabric showing the back side thereof with the adhesive layer omitted.
Figure 5:
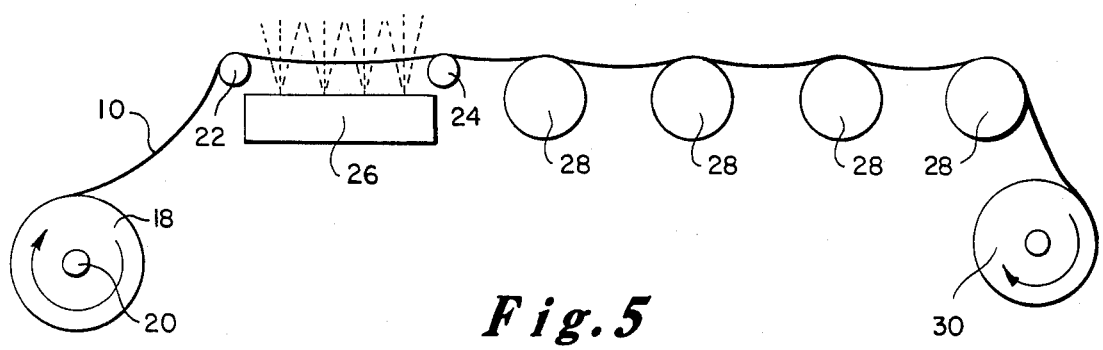
FIG. 5 is a schematic elevational view showing the conveying of the fabric web in a relaxed condition through a spray of steam, and then over low heat drying rolls, and then showing the rewinding of the fabric in a relaxed state.

The process begins, as shown in FIG. 5, by mounting a roll 18 of fabric 10 on a specially constructed roll stand 20 which is adapted to be precisely driven to pay off the continuous web of fabric 10 at a rate which will keep the fabric in a tensionfree, relaxed condition throughout the first processing step shown in FIG. 5. The fabric moves over two non-driven rolls 22 and 24 between which the fabric receives a spray of steam from a steam box 26. The steam spray is spread so that steam is directed against the entire surface of the fabric. Although not crucial, it is preferred to apply the steam spray to the back side of the fabric (the side shown in FIG. 2) in order to maximize the steam's effect on all of the non-stretch yarns and fibers.

The purpose of the steam application is to exfoliate and spread and loosen the cotton filling and cotton warp yarns and to spread and loosen the cotton fibers to permit the spandex core filaments to retract and contract to the maximum extent. This steaming step opens the pores and enhances the breathability of the fabric, especially when the fabric is stretched, and increases the capability of the fabric to be stretched for extended periods of time and to powerfully return to substantially its original length time after time. This steaming operation is not disclosed by the prior art Hoey patent and, as a result, applicants' bandaging material possesses superior breathability and superior snap-back and elasticity. Even after applicants' bandaging material has been stretched for a long time, it retains substantially all of its original snap-back and elasticity.

After steam has been applied to the relaxed fabric by steam box 26, the fabric 10 is further conveyed in a relaxed condition over drying means consisting of low heat rolls 28. After the fabric passes the last heated roll, the fabric has become almost completely dry and is then rewound on a specially constructed roll stand 30 which is designed to take up the fabric 10 in a relaxed condition. It will be understood that the drying means can take other forms so long as it does not raise the temperature of the fabric above approximately 235° F.

Applicants take great care (a) to avoid stretching their fabric and (b) to avoid applying high heat. By keeping the fabric relaxed throughout the entire process and by avoiding heating the fabric to above approximately 235° F., applicants ensure that their fabric retains its pronounced snap-back and elastic characteristics.

Figure 6:
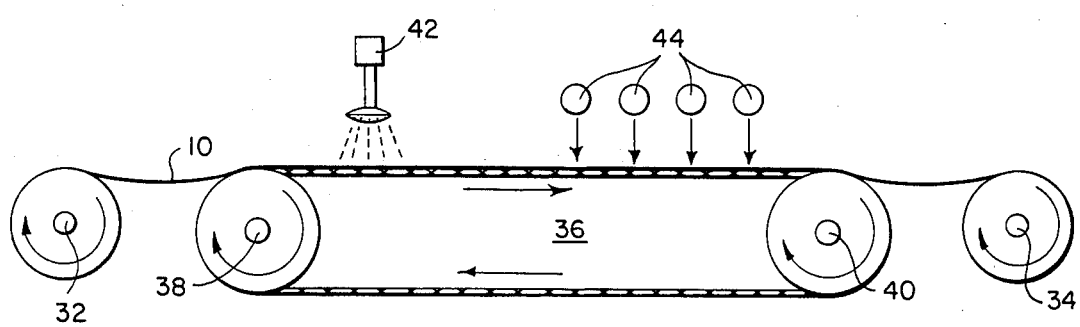
FIG. 6 is a schematic elevational view showing the conveying of the fabric web in a relaxed condition under a spray of a combined release and non-fray coating, and then under low heat drying elements, and then showing the rewinding of the fabric in a relaxed state.

The next processing operation is illustrated in FIG. 6. Although FIG. 6 is shown as a separate processing operation with relation to FIG. 5, this separation is not mandatory. Specifically, the two processing operations could be made contiguous. This would be accomplished by omitting take-up roll stand 30 (in FIG. 5) and pay-off roll stand 32 (in FIG. 6). Then, the fabric would run directly from the FIG. 5 operation to the FIG. 6 operation without being wound or unwound. The fabric would be kept in a relaxed condition throughout the steaming, drying, coating, and drying steps. At the end of FIG. 6, a take-up roll stand (like 30) would rewind the fabric 10 in a relaxed condition.

However, for purposes of clarity, FIG. 6 shows a pay-off roll stand 32 which is similar to the pay-off roll stand 20 in FIG. 5. The web of fabric 10, after leaving pay-off roll 32 in a relaxed condition, moves to a conveyor 36. The conveyor is driven by two rolls 38, 40 in the direction shown in FIG. 6. The surface of the conveyor belt is porous and the fabric lies on the upper run of the conveyor in a relaxed condition.

A spray head 42 is mounted above the conveyor and is arranged to spray the entire face side of the fabric with a fluid coating, the nature of which will be described subsequently. The spray head is preferably cam-driven so that it swings from side to side in a precisely timed manner causing the entire surface of the fabric to be covered with an equal amount of the sprayed fluid.

The sprayed fluid contains a release agent which aids in the unwinding of the roll of adhesive bandaging material. A good release agent is a water-borne silicone polymer. In addition, the sprayed fluid could advantageously also contain an acrylic polymer which stiffens the fabric making it easier to laterally tear by hand and which reduces the fraying of the edges of the fabric when the fabric is manually torn. The acrylic polymer prevents unraveling of the yarns during tearing, resists twisting of the yarns, gives more dimensional stability to the yarns, and gives the fabric a crisper "hand". The combined release agent and acrylic polymer constituents are sprayed in a latex form for ease of application to the fabric. Of course, the latex could be applied by means other than by a spray head.

After the latex has been sprayed on the face side of the fabric, the relaxed fabric is conveyed under a bank of low-heat drying elements 44. Then, the dried fabric is rolled up in a completely relaxed condition on roll stand 34, which is similar to roll stand 30.

It should be understood that the release agent and the non-fray agent can be combined and applied, or can be independently applied, and do not necesesarily have to be applied together or in sequence. They are independent, but it may be convenient to apply the two agents together. In fact, depending upon the nature of the yarns used, one or both agents could be omitted.

Figure 7:
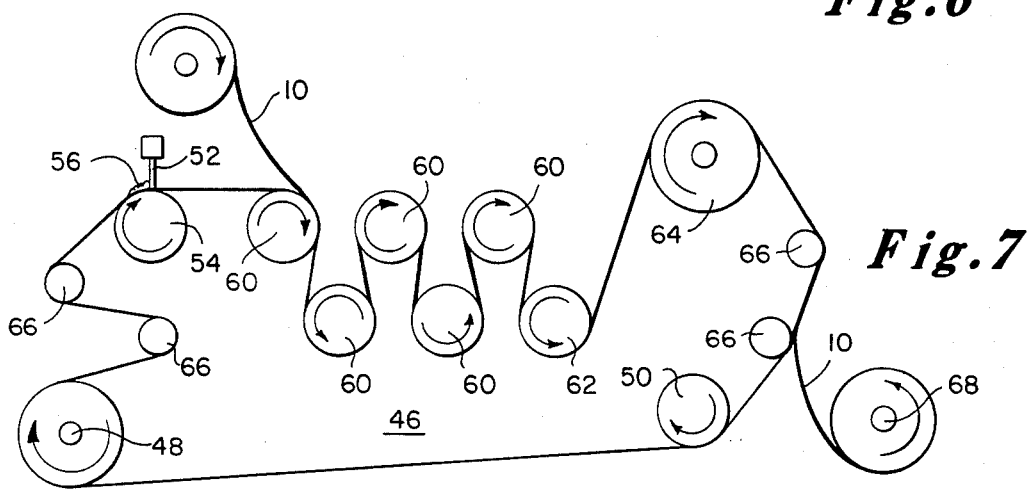
FIG. 7 is a schematic elevational view showing the drawing of adhesive under a blade-coating means, and then the application of the adhesive under very light pressure to a web of relaxed fabric, the drying of the adhesive under low heat conditions, and then the rewinding of the fabric in a relaxed state.

FIG. 7 shows the processing operation in which the adhesive is applied to the back side of the fabric. As previously stated with regard to the option of making contiguous the processing steps shown in FIGS. 5 and 6, the processing step shown in FIG. 7 can be made contiguous with the immmediately preceding and/or the immediately succeeding steps. However, for purposes of illustration, FIG. 7 shows a conveyor 46 which is driven by rolls 48 and 50. The conveyor belt has a release-coated surface and continuously travels in the direction shown in FIG. 7.

A doctor blade 52 is mounted over a coating roll 54 in conventional fashion such that the blade can be accurately adjusted to provide the desired spacing between the blade and the conveyor belt being carried by coating roll 54. The process operator manually (or with the aid of appropriate equipment) continuously or periodically applies a quantity of adhesive material 56 onto the conveyor belt immediately upstream of the doctor blade. The conveyor belt carries the adhesive material against and under the doctor blade which causes the adhesive material to be coated onto the conveyor belt in a level layer having a uniform depth. At the same time, the fabric 10, having been previously steamed (FIG. 5) and release and/or non-fray coated (FIG. 6), is unrolled from a roll stand 58 in a completely relaxed condition. The fabric 10 drops onto the conveyor belt which has been previously coated with the layer of adhesive by the doctor blade 52. Thus, the back side of the fabric is brought into contact with the level upper surface of the adhesive. The fabric is completely relaxed and the adhesive has a uniform depth and has a smooth and level upper planar surface (in contact with the back side of the fabric) and a smooth and level lower planar surface (in contact with the conveyor belt). The fabric and adhesive, in engagement with each other, are then conveyed over and around a series of steam containing rollers 60, an unheated roller 62, and a chilled roller 64, all for the primary purpose of causing the adhesive to strongly and permanently adhere to the back side of the fabric.

Small idler rollers 66 cooperate with the conveyor belt to keep the belt taut and to directionally guide it during its travel over and around the other rollers. After the web of fabric 10, to which the layer of adhesive now adheres, passes over chilled roller 64, it is peeled away from the release-coated conveyor belt by the take-up roll stand 68. The fabric is rolled up by roll stand 68 in a completely relaxed condition. Thus, it will be seen that the fabric has passed from roll stand 20 (shown in FIG. 5) to roll stand 68 (shown in FIG. 7) in a continuously relaxed condition.

The adhesive 56 used in this process is a pressure-sensitive, permanently tacky adhesive material. Preferably, the adhesive material is primarily rubber with various other constituents which increase the tackifying and anti-oxidizing properties of the material. The material preferably has a high viscosity and a high solids content and is dissolved in solvent. If it is desired to use the bandaging material primarily for the health care market, rather than for the athletic market, an adhesive material which is hypo-allergenic should be used. Such a hypoallergenic material could be formulated from a solvent-based or a water-based compound and such material could be applied to the back side of the fabric by the FIG. 7 process or by a different process, such as by spraying.

It is important to note that the adhesive material 56 is applied to the back side of the fabric 10 by a very light pressure contact. The conveyor belt is kept only taut enough to prevent slippage on the rollers, but is kept loose enough so that the belt gently urges the layer of adhesive only against the back side of the fabric and not up into the interstices of the relaxed fabric to any significant extent. By this method, the upper surface of the adhesive material remains virtually parallel to the lower surface of the adhesive material during the entire adhesive coating step and during the entire take-up step on roll stand 68.

Figure 8:
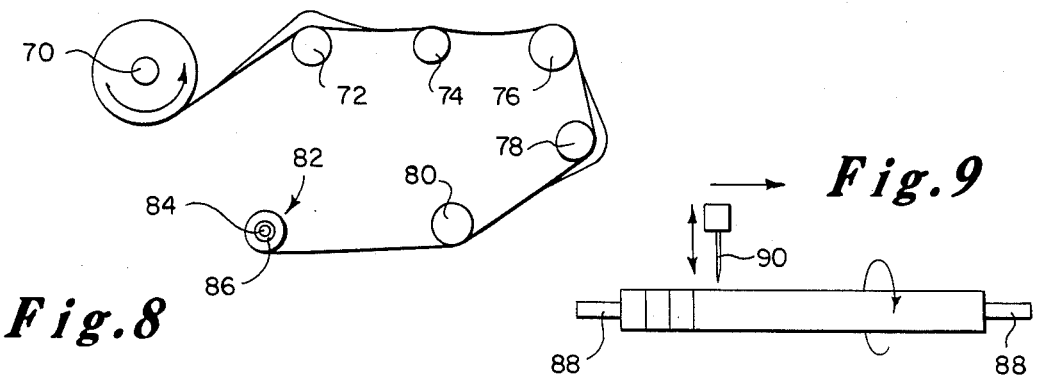
FIG. 8 is a schematic elevational view showing the conveying of the fabric web in a relaxed condition over several spreading rolls, and then showing the rewinding of the fabric on a core in a relaxed state so that the adhesive covered back side of the fabric is oriented inwardly towards the core and so that the release coated face side of the fabric is oriented outwardly away from the core.

The web of fabric 10, after being coated with adhesive and rolled up on roll stand 68, has its adhesive coated back side oriented away from the center of the roll and has its release agent coated face side oriented towards the center of the roll. The rolled fabric is in a relaxed condition which causes the rolled fabric to roll up into a very fat fabric roll on roll stand 68. Therefore, the necessary next step in the process, which is shown in FIG. 8, is the tensioned rewinding of the web of fabric onto a cardboard or other type of core. FIG. 8 shows the unrolling of the fabric from a driven roll stand 70. The fabric first passes over a non-driven bow roll 72 (such as Mount Hope roll) which laterally spreads the fabric and centers it on the roll surface. The spread fabric next proceeds to a non-driven roll 74 and then on to a driven pull roll 76 which has an adhesive covered surface for longitudinally pulling the fabric. The web of fabric next proceeds to another non-driven Mount Hope roll 78, then on to another non-driven roll 80, and finally onto a roll stand 82 which uses a long thin arbor 84, a long, small diameter cardbore core 86, and a driven take-up mechanism to slightly stretch and roll up the web of fabric on the core 86. In the rewinding operation, the ribbed face side of the web (containing the release coating) is positioned to face outwardly, and the back side of the web (containing the adhesive coating) is positioned to face inwardly.

Figure 9:
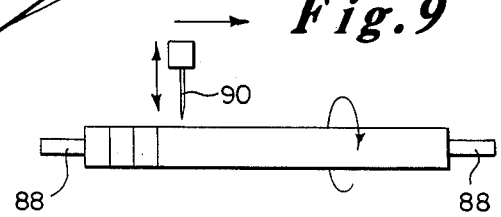
FIG. 9 is a top plan view showing the slitting of a roll of the bandaging material to the desired width.

Finally, as shown in FIG. 9, the arbor-carried cored roll of fabric is mounted in a lathe-like device, between two opposing spindles 88, and the roll of fabric is rotated. A rotating circular blade 90, on a movable swing arm, is programmed so that (a) it swings forward towards and into the roll of fabric a specified distance in order to slit the cored roll without contacting the arbor 84, (b) it swings back to its original position, and (c) it moves laterally a specified distance in order to set the desired roll width before the blade swings forward again to make the next slit in the cored roll. After the wide roll has been slit into a number of narrow rolls having the desired roll width, the spindles are spread, the arbor is removed from the lathe-like device, and the rolls of bandaging material are removed from the arbor. Each roll of material has the appearance of the roll shown in FIG. 1. This completes the description of the process of this invention.

The bandaging material of this invention will now be described in detail. The roll of material is shown in FIG. 1. It is rolled on a cardboard core 86, has its adhesive coated back side positioned towards the core, and has its release coated face side positioned away from the core. The bandaging material is made from a fabric 10 which is formed by essentially non-stretch filling yarns 12 interwoven with warp yarns consisting of stretch yarns 16 interspersed with essentially non-stretch yarns 14 in a weave such that the stretch warp yarns have a relatively long float length on the back side of the fabric and the non-stretch warp yarns have a relatively short float length on the back side of the fabric. This is clearly shown in FIG. 2 and causes the fabric to become extremely corrugated when in a relaxed condition (FIG. 3) and to become substantially planar when in a stretched condition (FIG. 4).

The fabric 10 has substantially open pores which were produced by the steaming operation. This increases the breathability of the bandaging material. The fabric also has powerful and long-lasting elastic stretch warp yarns, the power and the long-lasting nature of the stretch yarns being enhanced by the application of steam to the cotton yarns and fibers which loosens their grip on the elastomeric core filaments of the stretch yarns. The steaming increases the capability of the bandaging material to powerfully and fully recover over and over even after being stretched for long lengths of time.

Figure 3:
FIG. 3 is an elevational view, in cross-section, of a fabric in its relaxed condition, showing the non-stretched warp yarns extending towards and away from the back side of the fabric, showing the elastomeric stretch warp yarns extending along the back side of the fabric, and showing the adhesive layer on the back side of the fabric, the adhesive layer having a smooth level surface and a uniform depth.
Figure 4:
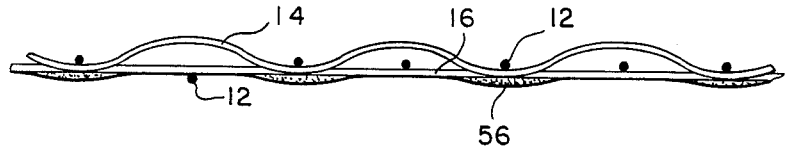
FIG. 4 is a similar schematic elevational view, in cross-section, of a fabric in its stretched condition, showing the adhesive layer having a non-uniform, discontinuous surface and a depth which is relatively great where the non-stretch warp yarns extend to the back side of the fabric and which is relatively slight or zero where the non-stretch warp yarns extend away from the back side of the fabric.

FIGS. 3 and 4 show what happens to the fabric when it is in the relaxed and the stretched conditions. FIG. 3 shows the fabric relaxed. The stretch warp yarn is planar and on the back side of the fabric. The non-stretch warp yarn 14 extends towards and away from the back side of the fabric. At the points where the non-stretch warp yarn 14 touches the back side of the fabric, it is in the same plane as the stretch warp yarn 16. This is clearly shown in FIG. 3. Also clearly shown is the uniform depth of adhesive material 56 and its smooth and flat lower exposed face. The adhesive material is attached to the relaxed fabric only at the back side of the fabric and does not extend upwardly to any significant extent into the interstices of the fabric.

FIG. 4 shows the fabric in its stretched condition. The stretch warp yarn 16 remains planar and remains on the back side of the fabric. The non-stretch warp yarn 14 has become closer to the fabric's back side, but still extends towards and away from the back side of the fabric. The major difference is that the adhesive layer 56 has assumed a quite different form. Its depth has become non-uniform and discontinuous. Where it touches the non-stretch warp yarns 14 at the back side of the fabric, it has retained its original depth. However, at all other locations, its depth has become shallower to varying degrees. In many locations, the adhesive layer is absent. If one were to hold the adhesive coated fabric up to the light, one would see that the adhesive layer was thickest where the non-stretch warp yarns 14 touch the back side of the fabric and was thinner or was absent everywhere else to varying degrees. Because of this variance of adhesive layer depth when the bandaging material is stretched, the material has superior breathability when wrapped around a person's arm or leg. This is an important characteristic and is produced to a great extent because the web of fabric is coated with adhesive when the fabric is in a relaxed condition. The combination of a ribbed fabric and a fabric coated in a relaxed condition strongly contributes to the breathability of and the air flow through the bandaging material which reduces irritations to and increases the comfort of the user.

The nature of the adhesive material has already been described. It has a smooth exposed surface and a substantially uniform depth throughout when the bandaging material is in a relaxed condition. When the bandaging material is stretched, the adhesive material has an undulating exposed surface and a depth which is relatively shallow or completely absent where the non-stretch warp yarns 14 extend away from the back side of the fabric and a depth which is relatively great where the non-stretch warp yarns extend to the back side of the fabric.

The nature of the release coating has also been already described. It is applied to the entire face side of the preferably relaxed fabric to improve the ability of the roll of bandaging material to be easily unwound. This release coating preferably contains an additional constituent which is an acrylic polymer that somewhat stiffens the material making it easier to tear off a piece of material and preventing the material edges from fraying during and after the tearing operation.

The resulting bandaging material is extremely breathable, tears quite easily, and hardly frays at the edges. It is most absorbent and has a strong and long-lasting power of recovery after long and numerous stretchings. Its adhesive coating and its release coating are both very effective. Some prior art competitive bandaging materials have limited recovery capability. Once stretched for a short while, they permanently lose their ability to powerfully retract to their original length. Not so with the present invention. Its power of recovery is extremely impressive.

These features of excellent breathability and great and long-lasting power of recovery are produced by the method's application of steam to the relaxed fabric and application of adhesive to the relaxed fabric. The method's advantages are maximized by the maintenance of the temperature of the fabric below approximately 235° F.

The above description obviously suggests many possible variations and modifications of this invention which would not depart from its spirit and scope. It should be understood, therefore, that the invention is not limited in its application to the details specifically described or illustrated and that, within the scope of the appended claims, it may be practiced otherwise than as specifically described or illustrated.

We claim:

1. A breathable, conformable, elastic, pressure-sensitive, permanently tacky, adhesive bandaging material comprising:
   (a) a fabric having face and back sides and formed by essentially non-stretch filling yarns interwoven with warp yarns, said warp yarns consisting essentially of non-stretch textile warp yarns interspersed with stretch warp yarns, said filling and warp yarns woven in a pattern such that said stretch warp yarns have an average float length on the back side of said fabric which exceeds the average float length of said non-stretch warp yarns on said back side, said fabric normally being in a relaxed condition; and
   (b) a pressure-sensitive, permanently tacky, adhesive applied in a level layer to the entire back side of said relaxed fabric to produce an adhesive bandaging material which in its relaxed state has an adhesive layer which has a smooth exposed surface and a substantially uniform depth throughout, and which in its stretched state has an adhesive layer which has a nonuniform, discontinuous surface and which has a depth which is relatively great where said non-stretch warp yarns extend to said back side of said fabric and which has a depth which is relatively slight or zero where said non-stretch warp yarns extend away from said back side of said fabric.

2. The bandaging material of claim 1 wherein each said stretch warp yarn has an elastomeric spandex core filament wrapped with essentially non-stretch fibers.

3. The bandaging material of claim 2 wherein said non-stretch yarns are cotton.

4. The bandaging material of claim 1 wherein said non-stretch yarns are cotton.

5. The bandaging material of claim 1 further including a coating applied to said face side of said fabric, said coating comprising a release agent to improve unwindability of a coiled roll of said bandaging material.

6. The bandaging material of claim 5 wherein said coating comprises a latex including a silicone release agent.

7. The bandaging material of claim 5 wherein said coating further comprises a non-fray agent to reduce fraying of the edges of said fabric during and after tearing.

8. The bandaging material of claim 7 wherein said coating comprises a latex including an acrylic polymer non-fray agent.

9. The bandaging material of claim 1 further including a coating applied to said face side of said fabric, said coating comprising a non-fray agent to reduce fraying of the edges of said fabric during and after tearing.

10. The bandaging material of claim 9 wherein said coating comprises a latex including an acrylic polymer non-fray agent.

11. The bandaging material of claim 1 wherein said adhesive is hypo-allergenic.

12. An assembly comprising a core onto which the bandaging material of Claim 1 is wound into a coiled roll.

13. A breathable, conformable, elastic, pressure-sensitive, permanently tacky, adhesive bandaging material comprising:
   (a) a dry fabric having face and back sides and formed by essentially non-stretch filling yarns interwoven with warp yarns, said warp yarns consisting essentially of non-stretch textile warp yarns interspersed with stretch warp yarns, said filling and warp yarns woven in a pattern such that said stretch warp yarns have an average float length on the back side of said fabric which exceeds the average float length of said non-stretch warp yarns on said back side, said fabric normally being in a relaxed, fully contracted condition with said interwoven filling and warp yarns being exfoliated and spread and with said non-stretch yarns expanded and loosened;
   (b) a dry coating on the entirety of said face side of said fabric, said coating comprising a release agent to improve unwindability of a coiled roll of said bandaging material; and
   (c) a dry pressure-sensitive, permanently tacky, adhesive in a level layer on the entire back side of said relaxed fabric, said adhesive bandaging material in its relaxed state having an adhesive layer which has a smooth exposed surface and a substantially uniform depth throughout and in its stretched state having an adhesive layer which has a non-uniform, discontinuous surface and a depth which is relatively great where said non-stretch warp yarns extend to said back side of said fabric and a depth which is relatively slight or zero where said non-stretch warp yarns extend away from said back side of said fabric.

14. A breathable, conformable, elastic, pressure-sensitive, permanently tacky, adhesive bandaging material comprising:
   (a) a dry fabric having face and back sides and formed by essentially non-stretched filling yarns interwoven with warp yarns, said warp yarns consisting essentially of non-stretch textile warp yarns interspersed with stretch warp yarns, said filling and warp yarns woven in a pattern such that said stretch warp yarns have an average float length on the back side of said fabric which exceeds the average float length of said non-stretch warp yarns on said back side, said fabric normally being in a relaxed, fully contracted condition with said interwoven filling and warp yarns being exfoliated and spread and with said non-stretch yarns expanded and loosened;
   (b) a dry coating on the entirety of said face side of said fabric, said coating comprising a non-fray agent to reduce fraying of the edges of said fabric during and after tearing;
   (c) a dry pressure-sensitive, permanently tacky, adhesive in a level layer on the entire back side of said relaxed fabric, said adhesive bandaging material in its relaxed state having an adhesive layer which has a smooth exposed surface and a substantially uniform depth throughout and in its stretched state having an adhesive layer which has a non-uniform, discontinuous surface and a depth which is relatively great where said non-stretch warp yarns extend to said back side of said fabric and a depth which is relatively slight or zero where said non-stretch warp yarns extend away from said back side of said fabric.

15. A breathable, conformable, elastic, pressure-sensitive, permanently tacky, adhesive bandaging material comprising:
   (a) a dry fabric having face and back sides and formed by essentially non-stretch filling yarns interwoven with warp yarns, said warp yarns consisting essentially of non-stretch textile warp yarns interspersed with stretch warp yarns, said filling and warp yarns woven in a pattern such that said stretch warp yarns have an average float length on the back side of said fabric which exceeds the average float length of said non-stretch warp yarns on said back side, said fabric normally being in a relaxed, fully contracted condition with said interwoven filling and warp yarns being exfoliated and spread and with said non-stretch yarns expanded and loosened;
   (b) a dry coating on the entirety of said face side of said fabric, said coating comprising a release agent, to improve unwindability of a coiled roll of said bandaging material, and a non-fray agent, to reduce fraying of the edges of said fabric during and after tearing; and
   (c) a dry pressure-sensitive, permanently tacky, adhesive in a level layer on the entire back side of said relaxed fabric, said adhesive bandaging material in its relaxed state having an adhesive layer which has a smooth exposed surface and a substantially uniform depth throughout and in its stretched state having an adhesive layer which has a non-uniform, discontinuous surface and a depth which is relatively great where said non-stretch warp yarns extend to said back side of said fabric and a depth which is relatively slight or zero where said non-stretch warp yarns extend away from said back side of said fabric.

16. The method of producing breathable, conformable, elastic, pressure-sensitive, permanently tacky, adhesive bandaging material from a fabric having face and back sides and which has been formed by interweaving essentially non-stretch filling yarns with warp yarns, said warp yarns consisting essentially of non-stretch warp yarns interspersed with stretch warp yarns, said filling and warp yarns woven in a pattern such that said stretch warp yarns have an average float length on said back side of said fabric which exceeds the average float length of said non-stretch warp yarns on said back side, said method comprising the following steps:

(a) conveying a continuous web of said fabric in a substantially relaxed condition and applying heat and moisture to said relaxed fabric to exfoliate and spread said interwoven filling and warp yarns and to expand and loosen said non-stretch yarns thereby facilitating a fuller contraction of said stretch yarns; and (b) applying a layer of pressure-sensitive, permanently tacky adhesive to said back side of said conveyed fabric while said conveyed fabric is in a substantially relaxed condition.

17. The method of claim 16 wherein said application of heat and moisture is an application of steam.

18. The method of claim 16 wherein said layer of adhesive is applied in a uniform depth to said back side of said fabric while said fabric is in a substantially relaxed condition.

19. The method of claim 18 wherein said step of applying a layer of adhesive to said back side of said conveyed fabric while it is in a substantially relaxed condition comprises applying a layer of adhesive to a conveyor by means of a doctor blade, contacting the exposed surface of said adhesive layer with said back side of said relaxed fabric and transferring said adhesive layer from said surface of said conveyor to said back side of said relaxed fabric to form a continuously smooth and level layer of adhesive on said back side of said fabric.

20. The method of claim 16 further including the step of applying a coating to said face side of said conveyed fabric, said coating comprising a release agent to improve unwindability of a coiled roll of said bandaging material.

21. The method of claim 20 wherein the temperature of said fabric during said method is maintained below approximately 235° F.

22. The method of claim 20 wherein said coating applied to said face side of said conveyed fabric comprises a latex including a silicone release agent.

23. The method of claim 20 wherein said coating applied to said face side of said conveyed fabric further comprises a nonfray agent to reduce fraying of the edges of said fabric during and after tearing.

24. The method of claim 26 wherein the temperature of said fabric during said method is maintained below approximately 235° F.

25. The method of claim 26 wherein said coating applied to said face side of said conveyed fabric comprises a latex including an acrylic polymer non-fray agent.

26. The method of claim 16 further including the step of applying a coating to said face side of said conveyed fabric, said coating comprising a non-fray agent to reduce fraying of the edges of said fabric during and after tearing.

27. The method of claim 26 wherein the temperature of said fabric during said method is maintained below approximately 235° F.

28. The method of claim 26 wherein said coating applied to said face side of said conveyed fabric comprises a latex including an acrylic polymer non-fray agent.

29. The method of claim 16 including the step of drying said conveyed fabric immediately after applying said heat and moisture.

30. The method of claim 29 including the steps, after drying said conveyed fabric immediately after applying said heat and moisture, of:

(a) applying a coating to said face side of said conveyed fabric, said coating comprising a release agent to improve unwindability of a coiled roll of said bandaging material; and (b) drying said conveyed fabric immediately after applying said coating;

(c) the temperature of said fabric during said method being maintained below approximately 235° F.

31. The method of claim 29 including the steps, after drying said conveyed fabric immediately after applying said heat and moisture, of:

(a) applying a coating to said face side of said conveyed fabric, said coating comprising a non-fray agent to reduce fraying of the edges of said fabric during and after tearing; and (b) drying said conveyed fabric immediately after applying said coating;

(c) the temperature of said fabric during said method being maintained below approximately 235° F.

32. The method of claim 29 including the steps, after drying said conveyed fabric immediately after applying said heat and moisture, of:

(a) applying a coating to said face side of said conveyed fabric, said coating comprising a release agent, to improve unwindability of a coiled roll of said bandaging material, and a non-fray agent, to reduce fraying of the edges of said fabric during and after tearing; and (b) drying said conveyed fabric immediately after applying said coating;

(c) the temperature of said fabric during said method being maintained below approximately 235° F.

33. The method of claim 16 further including the final steps of winding said conveyed fabric into a roll and slitting said roll into a plurality of rolls of predetermined roll width.

34. The method of claim 16 wherein said non-stretch yarns comprise cotton yarns.

35. The method of claim 16 wherein each said stretch yarn comprises a spandex filament core around which are wrapped fibers including cotton fibers.

36. The method of claim 16 wherein the temperature of said fabric during said method is maintained below approximately 235° F.

37. The method of claim 16 wherein said adhesive applied to said back side of said fabric is hypo-allergenic.

38. The method of producing breathable, conformable, elastic, pressure-sensitive, permanently tacky, adhesive bandaging material from a fabric having face and back sides and which has been formed by interweaving essentially non-stretch filling yarns with warp yarns, said warp yarns consisting essentially of non-stretch warp yarns interspersed with stretch warp yarns, said filling and stretch warp yarns woven in a pattern such that said stretch warp yarns have an average float length on said back side of said fabric which exceeds the average float length of said non-stretch warp yarns on said back side, said method comprising the following steps:

(a) conveying a continuous web of said fabric in a substantially relaxed condition and applying heat and moisture to said relaxed fabric to exfoliate and spread said interwoven filling and warp yarns and to expand and loosen said non-stretch yarns thereby facilitating a fuller contraction of said stretch yarns;

(b) drying said conveyed fabric immediately after applying said heat and moisture;

(c) applying a coating to the entirety of said face side of said conveyed and dried fabric, said coating comprising a release agent to improve unwindability of a coiled roll of said bandaging material;

(d) drying said coating comprising said release agent on said conveyed fabric immediately after applying said coating;

(e) applying a layer of pressure-sensitive, permanently tacky adhesive to said back side of said conveyed fabric while it is in a substantially relaxed condition; and (f) drying said adhesive layer on said conveyed fabric;

(g) the temperature of said fabric during said method being maintained below approximately 235° F.

39. The method of producing breathable, conformable, elastic, pressure-sensitive, permanently tacky, adhesive bandaging material from a fabric having face and back sides and which has been formed by interweaving essentially non-stretch filling yarns with warp yarns, said warp yarns consisting essentially of non-stretch warp yarns interspersed with stretch warp yarns, said filling and warp yarns woven in a pattern such that said stretch warp yarns have an average float length on said back side of said fabric which exceeds the average float length of said non-stretch warp yarns on said back side, said method comprising the following steps:

(a) conveying a continuous web of said fabric in a substantially relaxed condition and applying heat and moisture to said relaxed fabric to exfoliate and spread said interwoven filling and warp yarns and to expand and loosen said non-stretch yarns thereby facilitating a fuller contraction of said stretch yarns;

(b) drying said conveyed fabric immediately after applying said heat and moisture;

(c) applying a coating to the entirety of said face side of said conveyed fabric, said coating comprising a non-fray agent to reduce fraying of the edges of said fabric during and after tearing;

(d) drying said coating comprising said non-fray agent on said conveyed fabric immediately after applying said coating;

(e) applying a layer of pressure-sensitive, permanently tacky adhesive to said back side of said conveyed fabric while it is in substantially relaxed condition; and (f) drying said adhesive layer on said conveyed fabric;

(g) the temperature of said fabric during said method being maintained below approximately 235° F.

40. The method of producing breathable, conformable, elastic, pressure-sensitive, permanently tacky, adhesive bandaging material from a fabric having face and back sides and which has been formed by interweaving essentially non-stretch filling yarns with warp yarns, said warp yarns consisting essentially of non-stretch warp yarns interspersed with stretch warp yarns, said filling and warp yarns woven in a pattern such that said stretch warp yarns have an average float length on said back side of said fabric which exceeds the average float length of said non-stretch warp yarns on said back side, said method comprising the following steps:

(a) conveying a continuous web of said fabric in a substantially relaxed condition and applying heat and moisture to said relaxed fabric to exfoliate and spread said interwoven filling and warp yarns and to expand and loosen said non-stretch yarns thereby facilitating a fuller contraction of said stretch yarns;

(b) drying said conveyed fabric immediately after applying said heat and moisture;

(c) applying a coating to the entirety of said face side of conveyed fabric, said coating comprising a release agent, to improve unwindability of a coiled roll of said bandaging material, and a non-fray agent, to reduce fraying of the edges of said fabric during and after tearing;

(d) drying said coating comprising said release and non-fray agents on said conveyed fabric immediately after applying said coating;

(e) applying a layer of pressure-sensitive, permanently tacky adhesive to said back side of said conveyed fabric while it is in a substantially relaxed condition; and (f) drying said adhesive layer on said conveyed fabric;

(g) the temperature of said fabric during said method being maintained below approximately 235° F.

* * * * *